(12) United States Patent
Heindl et al.

(10) Patent No.: US 8,674,080 B2
(45) Date of Patent: Mar. 18, 2014

(54) DYE COMPOSITION FOR LIQUID TRANSFER CONTROL

(75) Inventors: Dieter Heindl, Paehl (DE); Waltraud Ankenbauer, Penzberg (DE); Hans-Peter Josel, Weilheim (DE); Christian Weilke, Penzberb (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 784 days.

(21) Appl. No.: 12/748,535

(22) Filed: Mar. 29, 2010

(65) Prior Publication Data

US 2010/0258742 A1    Oct. 14, 2010

(30) Foreign Application Priority Data

Apr. 9, 2009  (EP) .................................... 09005256
Aug. 4, 2009  (EP) .................................... 09167140

(51) Int. Cl.
*C07H 21/04*  (2006.01)
*G01N 21/62*  (2006.01)

(52) U.S. Cl.
USPC ........ 536/23.1; 73/61.41; 73/61.43; 73/61.48

(58) Field of Classification Search
None
See application file for complete search history.

(56) References Cited

U.S. PATENT DOCUMENTS

| | | | |
|---|---|---|---|
| 5,736,333 A | 4/1998 | Livak et al. | |
| 5,861,251 A | 1/1999 | Park et al. | |
| 6,830,889 B1 | 12/2004 | Matsumoto et al. | |
| 2004/0023207 A1* | 2/2004 | Polansky | 435/5 |
| 2007/0059752 A1* | 3/2007 | Cook | 435/6 |
| 2007/0077588 A1 | 4/2007 | Will | |

FOREIGN PATENT DOCUMENTS

| | | |
|---|---|---|
| WO | 00/14505 A1 | 3/2000 |
| WO | 2006/044994 A3 | 4/2006 |
| WO | 2007/039301 A3 | 4/2007 |
| WO | 2007/059816 A1 | 5/2007 |
| WO | 2007/070542 A3 | 6/2007 |
| WO | 2008/021446 A3 | 2/2008 |

OTHER PUBLICATIONS

Li et al. A new class of homogeneous nucleic acid probes based on specific displacement hybridization. Nuc Acids Res 30(2):e5 (9 pages) (2002).*
Baba et al. Ha-ras mutations in N-nitrosomorpholine-induced lesions and inhibition of hepatocarcinogenesis by antisense sequences in rat liver. Int J Cancer 72:815-820 (1997).*
Malicka et al. Enhanced emission of highly labeled DNA oligomers near silver metallic surfaces. Anal Chem 75:4408-4414 (2003).*
Fiandaca et al. Self-reporting PNA/DNA primers for PCR analysis. Genome Research 11:609-613 (2001).*
Ghosh et al. Real time kinetics of restriction endonuclease cleavage monitored by fluorescence resonance energy transfer. Nucleic Acids Research 22(15):3155-3159 (1994).*

(Continued)

*Primary Examiner* — Samuel Woolwine
(74) *Attorney, Agent, or Firm* — David J. Chang; Duane C. Marks; Marilyn L. Amick (57) ABSTRACT

The present invention provides kits and methods for composition ratio control based on dyes that are designed to enable energy transfer between each other. In more detail, with the method of the present invention it is possible to verify the mixing ratio of a first component comprising a first dye with a second component comprising a second dye.

14 Claims, 7 Drawing Sheets

(56) References Cited

OTHER PUBLICATIONS

European Search Report issued Jul. 23, 2009 in European Application No. 09005256.4.
Marme, Nicole et al., Single nucleotide polymorphism analysis using different colored dye dimer probes, Chemical Physics Letters, 2006, pp. 440-445, vol. 428.
Marras, Salvatore A. E., et al, Efficiencies of fluorescence resonance energy transfer and contact-mediated quenching in oligonucleotide probes, Nucleic Acids Research, 2002, 8 pages, vol. 30, No. 21, e122.
Nikiforov, Theo T. and Beechem, Joseph M., Development of homogeneous binding assays based on fluorescence resonance energy transfer between quantum dots and Alexa Fluor fluorophores, Analytical Biochemistry, 2006, pp. 68-76, vol. 357.
SRISA-ART, Monpichar et al., High-Throughput DNA Droplet Assays Using Picoliter Reactor Volumes, Analytical Chemistry, Sep. 1, 2007, pp. 6682-6689, vol. 79, No. 17.
Yanek, Melanie, Minimization of variance in QRT-PCT Optimization of QRT-PCR for sensitivity and user convenience, BIOspektrum, 2007, pp. 519-520, vol. 13, No. 5.

* cited by examiner

Figure 1 a) | unbound | bound

|   | I | II | | |
|---|---|---|---|---|
| i) | Dye | - Dye | $Ex\ \lambda_{II} \to Em\ \lambda_{II}$ | $Ex\ \lambda_I \to Em\ \lambda_{II}$ |
|   |   |   | or $Ex\ \lambda_I \to Em\ \lambda_I$ |   |
| ii) | Dye | - Quencher | $Ex\ \lambda_I \to Em\ \lambda_I$ | $Ex\ \lambda_I \to Em\ \lambda_I$ |
| iii) | N.-fl. dye | - Dye | $Ex\ \lambda_{II} \to Em\ \lambda_{II}$ | $Ex\ \lambda_I \to Em\ \lambda_{II}$ | b) | bound | bound

|   | I | II | | |
|---|---|---|---|---|
| i) | Dye | - Dye | $Ex\ \lambda_I \to Em\ \lambda_{II}$ | $Ex\ \lambda_{II} \to Em\ \lambda_{II}$ |
| ii) | N.-fl. dye | - Dye | $Ex\ \lambda_I \to Em\ \lambda_{II}$ | $Ex\ \lambda_{II} \to Em\ \lambda_{II}$ |

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer GAPDH

<400> SEQUENCE: 1
agccacatcg ctcagacac                                                19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      reverse primer GAPDH

<400> SEQUENCE: 2
gcccaatacg accaaatcc                                                19

<210> SEQ ID NO 3

```
<211> LENGTH: 10
<212> TYPE: DNA
<213> ORGANISM: Artificial Sequence
<220> FEATURE:
<223> OTHER INFORMATION: Description of Artificial Sequence: Synthetic
      control oligo A (L-nucleotides only)

<400> SEQUENCE: 3
cccacatcga                                                          10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      control oligo B (L-nucleotides only)

<400> SEQUENCE: 4
tcgatgtggg                                                          10
```

DYE COMPOSITION FOR LIQUID TRANSFER CONTROL

RELATED APPLICATIONS

This application claims priority to EP 09005256.4 filed Apr. 9, 2009 and to EP 09167140.4 filed Aug. 4, 2009, which are hereby incorporated by reference in their entirety.

SEQUENCE LISTING

The instant application contains a Sequence Listing which has been submitted via EFS-Web and is hereby incorporated by reference in its entirety. Said ASCII copy, created on Mar. 23, 2010, is named 25847US.txt, and is 1,312 bytes in size.

FIELD OF THE INVENTION

The present invention related to the field of fluid transfer processes used in real-time polymerase chain reactions (PCR). The processes are based on measurements of intensities of dyes within the fluid to be transferred. The methods make use of control dyes and quencher molecules for the fluid transfer controls.

BACKGROUND OF THE INVENTION

Dyes are already used as controls for assay set-ups that require pipetting of several components. These control concepts are based on dyes only within one component and detecting the secondary colour after mixture with other components.

Especially real-time PCR systems require an exact mixture of all reaction components for reliable and comparable quantification, because the amount of sample material, of primers/probes as well as of master mixes required for real time PCR particularly influence the quantification result.

PCR master mix with an inert dye is used to minimize pipetting errors and commercial products are available, such as RedTaq of Sigma Aldrich or AbsoluteBlue of ThermoScientific (Yanek, M., BIOspektrum 13(5) (2007) 519-520). Alternatively, the ingredients (such as, e.g., the polymerase) of the components may be labeled prior to mixing to obtain a visual control of the pipetting process. E.g., the RedTaq of Sigma Aldrich comprises a labeled polymerase. The U.S. Pat. No. 5,861,251 discloses lyophilized PCR reagents comprising a dye. Moreover, also the probe materials may be provided with a dye for visualization (WO 2000/014505). Fluorescent dyes such as ROX and ROX/FAM FRET pairs are used as calibration standards (U.S. Pat. No. 5,736,333).

Currently, there are no control systems known in the state of the art that provide a volume control for more than one component to be mixed for a certain assay. Especially for real-time PCR systems the control dye must be optimized such that the detection dye of the real-time PCR is not affected and consequently, the adsorption of the control dye should not overlap with the detection channels used for monitoring the PCR and the control dye should be detected in a separate channel. This becomes more difficult, if two or more control dyes should be used, because the spectral window for PCR monitoring is reduced in order to avoid cross talk with respect to all control dyes.

The present invention provides a closed system for assay set-up that encompasses control strategies to identify volume errors of at least two components to be mixed for said assays.

SUMMARY OF THE INVENTION

One aspect of the present invention is a kit for composition ratio control, said kit comprising a) a first dye having a first affinity group, said first dye being excitable by a first excitation light to emit radiation or to transfer energy to a second dye, and b) a second dye having a second affinity group, said second dye being excitable by a second excitation light or by energy transfer from said first dye, characterized in that said first dye and said second dye are configured such that said first and said second affinity group have affinity to bind to each other, wherein energy transfer between said dyes is enabled upon binding of said first affinity group to said second affinity group and a mixture of said first dye and said second dye emits radiation upon excitation with said first or said second excitation light, wherein said radiation is a measure for the composition ratio of said first and said second dye.

The phrase "energy transfer" is used throughout the present invention to summarize all non-radiation energy transfers known to someone skilled in the art. A well known embodiment of such an energy transfer is the Fluorescence resonance energy transfer (FRET). Here, a donor chromophore, initially in its electronic excited state, may transfer energy to an acceptor chromophore (in close proximity, typically <10 nm) through non-radiative dipole-dipole coupling.

Another possible energy transfer is the photo-induced electrone transfer (PET). In this process electrons are accepted from or donated to the excited state of an excited fluorescent dye, which results in formation of a radical ion pair which returns to the ground state via radiationless charge recombination.

Depending on the used types of dyes, the binding of said first and said second affinity group can be reversible or irreversible throughout the present invention.

Throughout the present invention the radiation emitted by the dye mixture upon excitation with excitation light can be the radiation of the excited dye itself or the radiation of the other dye not excited by the excitation light, but excited indirectly by energy transfer from the initially excited dye.

The phrase "dye" is used to summarize all kinds of light adsorbing molecules and therefore, comprises fluorescent dyes, non-fluorescent dyes and quencher molecules.

Quencher molecules are capable of quenching the fluorescence of fluorescent dyes as they are excitable by fluorescent light and dispense energy, e.g., by heat. Non-fluorescent dyes (also named dark donor molecules) are dyes substantially without fluorescence emission in contrast to conventional fluorescent dyes.

Moreover, also aromatic or heteroaromatic structures that have quenching properties for fluorescence emission can be used for the present invention. These molecular structures are capable to adsorb energy from fluorescent dyes via a photo-induced electron transfer (PET) process. Examples for heteroaromatic structures are, e.g., simple molecular structures like guanine, deazaguanine (see Example 2) or iso guanosin that can be added to affinity groups, too.

Also indol derivatives like tryptophan in proteins or nitroindol incorporated as desoxyribosid derivative are well known compounds which have quenching properties. Moreover, nitroaromates like 2,4 dinitrophenylaniline derivatives which are commercially available as labeling reagents for oligonucleotide (as phosphoramidte) and protein labeling (as NHS esters) are also capable of quenching fluorophors.

Therefore, another aspect of the present invention is a kit for composition ratio control, said kit comprising a) a fluorescent dye having a first affinity group, said first dye being excitable by a first excitation light to transfer energy to an aromatic or heteroaromatic structure, and b) an aromatic or heteroaromatic structure having a second affinity group, said aromatic or heteroaromatic structure being excitable by energy transfer from said first dye, such that said aromatic or heteroaromatic structure prevents fluorescence emission of said fluorescent dye
characterized in that said first dye and said aromatic or heteroaromatic structure are configured such that
said first and said second affinity group have affinity to bind to each other, wherein energy transfer between said dye and said aromatic or heteroaromatic structure is enabled upon binding of said first affinity group to said second affinity group and
a mixture of said first dye and said aromatic or heteroaromatic structure emits radiation upon excitation with said first excitation light, wherein said radiation is a measure for the composition ratio of said first dye and said aromatic or heteroaromatic structure.

Throughout the present invention the dyes of the kit according to the present invention can be added to components that need to be mixed for a subsequent reaction and the composition ratio control in this case is directed to the composition of said components. Such components are, e.g., reagents, buffers, biological components or samples.

Yet another aspect of the present invention is a kit for composition ratio control comprising
a) a first component comprising a first dye having a first affinity group, said first dye being excitable with excitation light to emit radiation or transfer energy to another component, and
b) a second component comprising a second dye having a second affinity group, said second dye being excitable with radiation or by energy transfer from said first dye,
characterized in that said first component and said second component are to be combined in a predefined composition ratio,
wherein said composition ratio is controllable via measurement of radiation emitted by said dyes upon excitation with excitation light and
wherein said first and said second affinity group are designed to bind to each other, wherein energy transfer between said dyes is enabled upon binding of said first affinity group to said second affinity group.

Such a kit according to the present invention summarizes all kinds of kits having several components that need to be mixed prior to performing a certain production process or analytical assay. Consequently, such a kit has at least two components that each comprise a certain dye, whereas said components are, e.g., reagents, buffers or biological compounds.

Still another aspect of the present invention is a dye composition with composition ratio depending light emission, said dye composition comprising
a) a first dye having a first affinity group, said first dye being excitable with excitation light to emit radiation or transfer energy to another component, and
b) a second dye having a second affinity group, said second dye being excitable with radiation or by energy transfer from said first dye,
characterized in that said first dye and said second dye are provided such that
said first and said second affinity group have affinity to bind to each other, wherein energy transfer between said dyes is enabled upon binding of said first affinity group to said second affinity group and
the radiation emitted by the dye composition upon excitation with excitation light is a measure for the composition ratio of said first dye and said second dye.

Yet another aspect of the present invention is a method of verifying the composition ratio of two components using the kit according to the present invention, said method comprises the steps
a) mixing the two components, wherein the first component comprises the first dye having said first affinity group and the second component comprises the second dye having said second affinity group,
b) performing a first radiation measurement upon excitation with excitation light under conditions such that said first dye and said second dye are not bound to each other via said affinity groups,
c) performing a second radiation measurements upon excitation with excitation light under conditions such that said first dye and said second dye are bound to each other via said affinity groups, and
d) comparing the two radiation measurements of step b) and c) to verify the composition ratio of said two components.

The method described above is outlined with respect to mixing of two components, but the person skilled in the art will appreciate that the method can also be used for more components. E.g., it is possible to use a third component comprising a third dye, said third dye needs to have a different radiation wavelength compared to the first and second dye. If the ratio of four components need to be verified, two kits according to the present invention can be used such that the first and the second dye have affinity to bind to each other, whereas the third dye has only affinity to bind to the fourth dye.

If this embodiment of the method according to the present invention is performed along the progression of the steps a)-d), the dyes need to be in the bound as well as in the unbound state after the mixing and therefore, the binding of the two respective affinity groups have to be reversible.

Still another aspect of the present invention is a method of verifying the composition ratio of two components using the kit according to the present invention, said method comprises the steps
a) mixing the two components, wherein the first component comprises the first dye having said first affinity group and the second component comprises the second dye having said second affinity group,
b) performing a first radiation measurement upon excitation with excitation light under conditions such that said first dye and said second dye are bound, said first fluorescence measurement is performed applying excitation wavelengths specific for said second dye and measuring the emission intensity of said second dye and
c) performing a second radiation measurement upon excitation with excitation light under conditions such that said first dye and said second dye are bound, said second fluorescence measurement is performed applying excitation wavelengths specific for said first dye and measuring the emission intensity of said second dye, and
d) comparing the two radiation measurements of step b) and c) to verify the composition ratio of said two components.

In this method according to the present invention both radiation measurements are performed with the dyes bound to each other via their affinity groups. Consequently, here it is possible, but not essential that the binding of the two respective affinity groups can be irreversible.

As mentioned before, also aromatic or heteroaromatic structures can be used instead of dyes and therefore, another aspect of the present invention is a method of verifying the composition ratio of two components using the kit according to the present invention, said method comprises the steps a) mixing the two components, wherein the first component comprises the fluorescent dye having said first affinity group and the second component comprises the aromatic or heteroaromatic structure having said second affinity group, b) performing a first radiation measurement upon excitation with excitation light under conditions such that said fluorescent dye and said aromatic or heteroaromatic structure are not bound to each other via said affinity groups, said first radiation measurements is performed applying excitation wavelengths specific for said fluorescent dye and measuring the emission intensity of said fluorescent dye, c) performing a second radiation measurements upon excitation with excitation light under conditions such that said fluorescent dye and said aromatic or heteroaromatic structure are bound to each other via said affinity groups, said second radiation measurements is performed applying excitation wavelengths specific for said fluorescent dye and measuring the emission intensity of said fluorescent dye, and d) comparing the two radiation measurements of step b) and c) to verify the composition ratio of said two components.

DETAILED DESCRIPTION OF THE INVENTION

One aspect of the present invention is a kit for composition ratio control, said kit comprising a) a first dye having a first affinity group, said first dye being excitable by a first excitation light to emit radiation or to transfer energy to a second dye, and b) a second dye having a second affinity group, said second dye being excitable by a second excitation light or by energy transfer from said first dye, characterized in that said first dye and said second dye are configured such that said first and said second affinity group have affinity to bind to each other, wherein energy transfer between said dyes is enabled upon binding of said first affinity group to said second affinity group and a mixture of said first dye and said second dye emits radiation upon excitation with said first or said second excitation light, wherein said radiation is a measure for the composition ratio of said first and said second dye.

Figure 1:
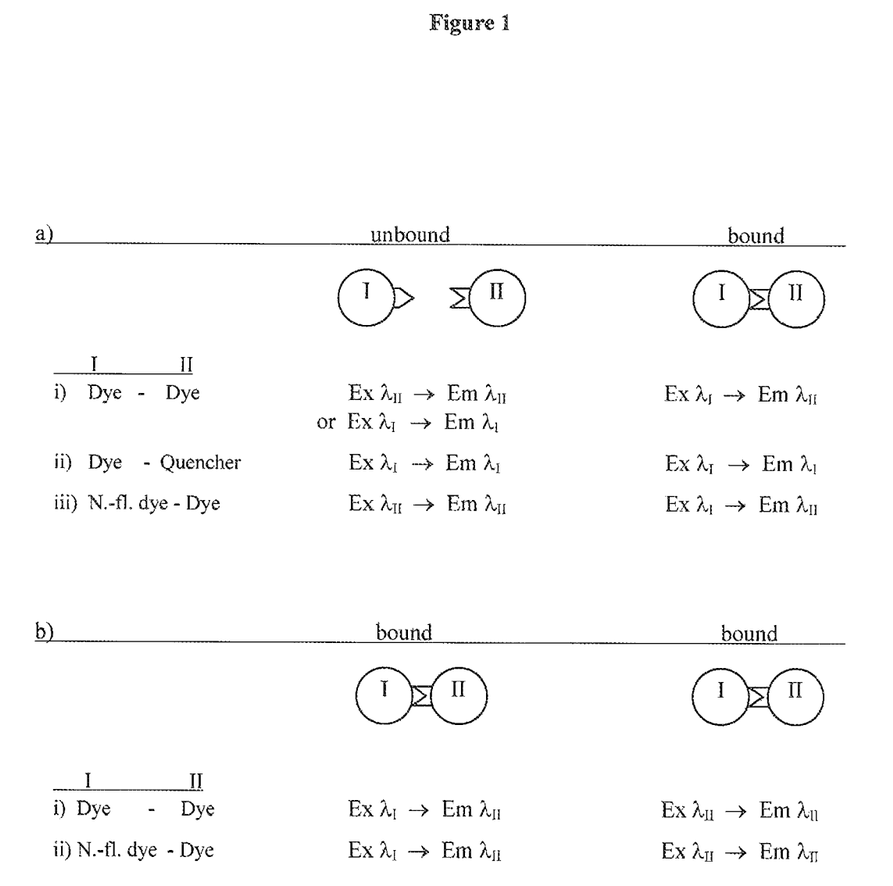
FIG. 1 Different embodiments of the present invention based on a) an unbound as well as a bound measurement and b) both measurements in bound state.

In the following a number of preferred affinity groups are described that are suitable for the kit according to the present invention. As illustrated in FIG. 1, the dyes with their affinity groups are all designed such that the dyes bind directly to each other via the affinity groups. Consequently, throughout the present application the binding of affinity groups to each other must be understood as a direct or specifical binding to each other and therefore, the indirect binding of the affinity groups via a third molecule is not part of the present invention.

A preferred kit according to the present invention is a kit, wherein said first affinity group is a biotin group and said second affinity group is a streptavidin group.

Another preferred kit according to the present invention is a kit, wherein said first affinity group is a digoxigenin group and said second affinity group is an anti-digoxigenin antibody.

Yet another preferred kit according to the present invention is a kit, wherein said first affinity group is a lectine and said second affinity group is a sugar.

Another preferred kit according to the present invention is a kit, wherein said first affinity group is an antibody and said second affinity group is a hapten.

Still another preferred kit according to the present invention is a kit, wherein said first affinity group is a first oligonucleotide and said second affinity group is a second oligonucleotide being complementary to said first oligonucleotide.

Using oligonucleotides as affinity groups is preferred, because it is easy to switch between the bound and the unbound state of these molecules by adjusting the solution temperature to above or below the melting temperature of the respective hybrid.

Throughout the present invention the term oligonucleotide is used to include DNA RNA and also oligonucleotide analogs, whereby the only prerequest is that such analogs are still capable of forming a stable duplex with each other. Such oligonucleotide analogs could compromise different modifications.

One class of analogs are derivatives of the natural nucleotides dA,dG,dC,dT,dU with substituents on the nucleobase. Examples are:

5-substituted pyrimidines, such as 5-methyl-dC, 5-aminoallyl-dU or -dC, 5-(aminoethyl-3-acrylimido)-dU, 5-propinyl -dU or -dC, 5 halogenated-dU and dC, N4 substituted cytidines, eg N4-ethyl-dC, N substituted purines, eg N6-ethyl-dA, N2 ethyl-dG, 8 substituted purines, eg 8-[6-amino)-hex-1-yl]-8-amino-dG or dA, 8 halogeno-dA or -dG, 8-alkyl dG or dA, or 2 substituted dA, such as 2 amino-dA.

One class of analogs are derivatives of the natural nucleotides dA, dG, dC, dT, dU with substituents on the d ribose moiety. Examples are:

2' methoxy, 2' fluoro, 2' methylseleno dU, 2' allyloxy, 4' methyl dU, dT; dU, dA, dG.

Another class are analogs wherein other nucleobases (non-standard) than the standard bases A, G, C, T, U are linked to the deoxy ribose sugar moiety or where the standard bases are linked to a sugar analog or a combination of both, wherein other nucleobases than the standard bases are linked to a sugar analog.

Examples for non-standard bases linked to d ribose are: 5-nitroindol-drib, 3 nitro pyrrole-drib, 7-deaza-dG and -dA, -dI, -dX, 7-deaza-8-aza-dG and -dA, -dI, -dX, 8-aza-dA, -dG, -dI, -dX, dFormycin, pseudo-dU. Pseudo-iso-dC, 4-thio-dT, 6-thio-dG, 2-Thio-dT, iso-dG, 5-methyl-iso-dC, 5,6-dihydro-5-aza-dC, etheno-dA, pyrollo-dC.

Sugar analogs are selected from: Xylose, 2',4' bridged Ribose like 2'-O, 4'-C methylene (oligomer known as LNA) or 2'-O, 4'-C ethylene (oligomer known as ENA), L-2 deoxyribose, hexitol (oligomer known as HNA), cyclohexen (oligomer known as CeNA), altritol (oligomer known as ANA), tricyclic ribose analog where C3' and C5' atoms are connected by an ethylene bridge that is fused to a cyclopropane ring (oligomer known as tricycloDNA), glycerin (oligomer known as GNA), Glucopyranose (oligomer known as Homo DNA), carbaribose (with a cyclopentan instead of tetrahydrofuran subunit) and Morpholin (oligomers known as morpholino DNA).

Such nucleotides analogs could be further derivatized, eg 7-propargyl-7-deaza G, or 5-aminoallyl-hexitol-U, 2'-fluoro-d(L)-Ribose.

A further class of analogs are oligonucleotides, where the internucleosidic phosphate bridge is modified like in phosphorthioate-methylphosphonate- or phosphoramidate oligonucleotides.

Another class of oligonucleotides compromise a backbone with peptide bonds, a well known example is PNA. PNA's backbone is composed of repeating N-(2-aminoethyl)-glycine units linked by peptide bonds.

If the ratio depending light emission of the dye mixture according to the present invention is used to verify the ratio of components for a subsequent PCR amplification, it is especially preferred to use L-nucleotides for the affinity groups. Such L-nucleotides having the L-conformation of the sugar instead of the D-conformation of natural nucleotides, still provide their hybridization properties, but the polymerase does no longer recognize these molecules. Consequently, such L-nucleotides can still be used as affinity groups without potentially affecting PCR reactions.

The same orthogonal effect as described above for L-nucleotides can be achieved using GNAs, homo DNA, and oligonucleotides which compromise orthogonal base pairs (like iso dG and iso dC)

A more preferred kit according to the present invention is a kit, wherein said oligonucleotides are composed of L-nucleotides.

Throughout the present invention several combinations of dyes can be used and in the following some suitable combination are described without limiting the scope of the present invention. Different combinations of said first dye (I) and said second dye (II) are illustrated in FIG. 1, wherein FIG. 1a comprises the embodiments that need said dyes in the unbound (left) as well as in the bound (right) state and wherein FIG. 1b comprises the embodiments that need said dyes only in the bound state.

A preferred kit according to the present invention is a kit, wherein said first dye is a fluorescent dye and said second dye is a quencher molecule, said quencher molecule being excitable by energy transfer from said fluorescent dye upon binding of the affinity groups, such that said quencher molecule prevents fluorescence emission of said fluorescent dye.

A special case of this quenching embodiment is the so-called self-quenching set-up, where said fluorescent dye and said quencher molecule are the same molecules and one fluorescent dye is quenched by another. This self-quenching occurs via a dye-dye interaction which is induced by bringing the dye molecules in close proximity, e.g., by increasing the dye concentration over a certain limit. Most of the fluorescent dyes provide this self-quenching properties, especially Rhodamines, Bora diazaindacenes, (known as Bodipy-dyes) Cyanines, Fluoresceines or Oxazines.

Therefore, another preferred kit according to the present invention is a kit, wherein said fluorescent dye and said quencher molecule are the same molecule.

In this embodiment of the present invention the fluorescent dye will be excited with excitation light having a suitable wavelength (Ex $\lambda_I$) and the fluorescence emission of said fluorescent dye (Em $\lambda_I$) will be monitored (FIG. 1a/ii). In case that the fluorescent dye and the quencher molecule are not bound to each other fluorescence emission (Em $\lambda_I$) will be detected and the intensity of the emission is a measure for the amount of fluorescent dye. If the fluorescent dye and the quencher molecule are bound to each other, the fluorescence emission will be quenched by the quencher molecule. Consequently, the fluorescence emission (Em $\lambda_I$) will be reduced and the intensity reduction is a measure of the amount of quencher molecules.

Another preferred kit according to the present invention is a kit, wherein said first dye is a first fluorescent dye and said second dye is a second fluorescent dye, said second fluorescent dye having an excitation maximum at a longer wavelength than said first fluorescent dye and wherein said second fluorescent dye being excitable by energy transfer from said first fluorescent dye upon binding of the affinity groups, such that said second fluorescent dye emits fluorescence light having a wavelength different from the wavelength of said first fluorescent dye.

In this embodiment two fluorescent dyes are used having different excitation wavelength. In case of bound affinity groups, using the specific excitation of the first fluorescent dye (Ex $\lambda_I$, nearly no direct excitation of the second fluorescent dye) an energy transfer occurs to the second fluorescene dye, such that the specific fluorescence emission of the second fluorescent dye (Em $\lambda_{II}$) becomes detectable (FIG. 1a/i). On the other hand, no fluorescence emission specific to the second fluorescent dye (Em becomes detectable with unbound affinity groups upon excitation with Ex $\lambda_I$, but Em $\lambda_{II}$ only becomes detectable using Ex $\lambda_{II}$ as excitation. Consequently, the fluorescence emission will be a measure for the ratio of the first and the second fluorescent dye.

Still another preferred kit according to the present invention is a kit, wherein said first dye is a non-fluorescent dye and said second dye is a fluorescent dye, said fluorescent dye being excitable by energy transfer from said non-fluorescent dye upon binding of the affinity groups, such that said fluorescent dye emits fluorescence light.

This embodiment is similar to the embodiment with two fluorescent dyes described before, only that the non-fluorescent dye upon excitation with its specific excitation (Ex $\lambda_I$) substantially does not emit a specific fluorescence emission by itself. The term non-fluorescent dye is used throughout the present invention analogous to the description of the US 2007/0077588, namely a non-fluorescent dye is a dye substantially without fluorescence emission in contrast to conventional fluorescent dyes that emit most of their energy via fluorescence. Only in case of bound affinity groups the specific fluorescence emission of the second fluorescent dye (Em $\lambda_{II}$) becomes detectable, if upon specific excitation of the first non-fluorescent dye using its specific excitation wavelength (Ex $\lambda_I$, nearly no direct excitation of the second fluorescent dye) an energy transfer occurs to the second fluorescene dye emitting the specific fluorescence emission of the second fluorescent dye (Em $\lambda_{II}$, FIG. 1a/iii). In case of unbound affinity groups, no fluorescence emission specific to the second fluorescent dye becomes detectable upon excitation with Ex $\lambda_I$, but Em $\lambda_{II}$ only becomes detectable using Ex $\lambda_{II}$ as excitation. Consequently, the fluorescence emission will be a measure for the ratio of the non-fluorescent dye and the fluorescent dye. Such non-fluorescent dyes can also be specified as dark donor molecules.

As mentioned before the dyes of the kit according to the present invention can be added to components that need to be mixed for a subsequent reaction and the composition ratio control in this case is directed to the composition of said reaction components. Consequently, said reaction components may be part of the kit according to the present invention.

A preferred kit according to the present invention further comprising a first reaction component.

In order to use the dyes of said kit for a composition ratio control of said reaction component and a sample that is not part of the kit, it is necessary to add one dye to said sample and the other dye need to be within said reaction component. Throughout the present invention a reaction component with a dye can be provided in at least two different ways.

In a more preferred kit according to the present invention, said first reaction component comprises said first dye.

In another more preferred kit according to the present invention, said first dye is addable to said first reaction component prior to use of said first reaction component.

Another preferred kit according to the present invention further comprising a second reaction component, said second reaction component optionally comprises said second dye.

The person skilled in the art will appreciate that many different kits comprising dyes and reaction components are within the scope of the present invention and in the following several of those kids are outlined as examples.

A preferred kit according to the present invention is a PCR kit, wherein said first reaction component is a master mix comprising said first dye and said second reaction component is a buffer solution comprising said second dye to be added to a sample, said sample comprising the target to be amplified. Alternatively, the first or second reaction component can be a detection mix required for said PCR.

Another preferred kit according to the present invention is a sample preparation kit, wherein said first reaction component is a lysis/binding buffer comprising said first dye and said second reaction component is a magnetic bead solution comprising said second dye. Alternatively, the first or second reaction component is a buffer solution comprising said second dye to be added to a sample solution.

Another preferred kit according to the present invention is an immuno assay kit, wherein said first reaction component is a specific antibody comprising said first dye and said second reaction component is a antibody conjugate for detection comprising said second dye. Alternatively, the first or second reaction component is a buffer solution comprising said second dye to be added to a sample solution.

As mentioned before, also certain molecular structures (like aromatic or heteroaromatic structures) can be used as quenching compounds for the present invention as long as they have quenching properties for fluorescence emission (see Example 2).

Therefore, another embodiment according to the present invention is a kit for composition ratio control, said kit comprising
  a) a fluorescent dye having a first affinity group, said first dye being excitable by a first excitation light to transfer energy to an aromatic or heteroaromatic structure, and
  b) an aromatic or heteroaromatic structure having a second affinity group, said aromatic or heteroaromatic structure being excitable by energy transfer from said first dye, such that said aromatic or heteroaromatic structure prevents fluorescence emission of said fluorescent dye characterized in that said first dye and said aromatic or heteroaromatic structure are configured such that
  said first and said second affinity group have affinity to bind to each other, wherein energy transfer between said dye and said aromatic or heteroaromatic structure is enabled upon binding of said first affinity group to said second affinity group and
  a mixture of said first dye and said aromatic or heteroaromatic structure emits radiation upon excitation with said first excitation light, wherein said radiation is a measure for the composition ratio of said first dye and said aromatic or heteroaromatic structure.

A preferred kit according to the present invention is a kit, wherein said first affinity group is a first oligonucleotide and said second affinity group is a second oligonucleotide being complementary to said first oligonucleotide.

Another preferred kit according to the present invention is a kit, wherein said oligonucleotides are composed of L-nucleotides.

Yet another preferred kit according to the present invention is a kit, wherein said heteroaromatic structure is a structure comprising guanine, deazaguanine, iso guanine or 7 deaza iso guanine. A more preferred kit according to the present invention is a kit, wherein said heteroaromatic structure are nucleotides with guanine or 7-deazaguanine as nucleobase. A even more preferred kit according to the present invention is a kit, wherein more than one nucleotide is combined to a homooligomeric oligonucleotide, e.g., (dG)3 (also written in the context of oligonucleotide sequences as GGG) or (7-deaza dG)3. Alternatively nitroindol desoxyriboside (a well known universal base) or homooligomers thereof are usable as quenching compounds.

Yet another aspect of the present invention is a method of verifying the composition ratio of two components using the kit according to the present invention, said method comprises the steps
  a) mixing the two components, wherein the first component comprises the first dye having said first affinity group and the second component comprises the second dye having said second affinity group,
  b) performing a first radiation measurement upon excitation with excitation light under conditions such that said first dye and said second dye are not bound to each other via said affinity groups,
  c) performing a second radiation measurements upon excitation with excitation light under conditions such that said first dye and said second dye are bound to each other via said affinity groups, and
  d) comparing the two radiation measurements of step b) and c) to verify the composition ratio of said two components.

In order to perform this embodiment of the method of verifying the composition ratio of two components according to the present invention, it is essential to measure radiation with the two dyes in bound as well as in unbound state. If the steps of said method are performed along the progression of the steps a)-d) above, it is necessary that the binding of the two affinity groups is reversible. Depending on the used affinity groups the person skilled in the art will know about procedures to allow or prevent the binding.

As mentioned before with respect to the kit embodiments of the present invention, the affinity groups are all designed to realize a direct binding of the dyes to each other via a specifically binding of their affinity groups (see FIG. 1). Moreover, the person skilled in the art will appreciate that this specifical binding of the affinity groups to each other is essential to perform the methods of the present invention, because otherwise a certain part of the dyes may bind to other ingredients of the components such that they are no longer available for the ratio control measurement and this will produce false results. Consequently, the affinity groups of the present invention are designed such that no interference with other ingredients of the components, but only a specifical binding to each other occurs. Therefore, the person skilled in the art will appreciate that said first dye and said second dye must bind specifically to each other via said affinity groups, if the right conditions are met. In another preferred method according to the present invention, said first radiation measurements of step b) is performed at composition parameters, such that the binding between said first affinity group and said second affinity group is prevented.

Throughout the present invention composition parameters that can be adjusted are, e.g., temperature, pH or molarity of the composition. In a preferred embodiment using oligonucleotides as affinity groups, the binding can be triggered by adjusting the composition temperature, such that the temperature is above or below the melting temperature of the respective hybrid.

Alternatively, the progression of the steps a)-d) above can be modified such that the first radiation measurement is performed prior to the mixing of both components. This embodiment has the advantage that also affinity groups having an irreversible binding can be used.

In a preferred method according to the present invention, said first radiation measurements of step b) is performed with said first component prior to mixing the two components in step a).

Depending on the dyes used for the present invention several different combinations of excitation and emission wavelength can be used.

In yet another preferred method according to the present invention, said first radiation measurements of step b) is performed applying excitation wavelengths specific for said first dye and measuring the emission intensity of said first dye.

This first radiation measurement can be performed with only the first dye present or with both dyes present in the unbound state. For an embodiment using a non-fluorescent dye, there is no detectable emission intensity upon excitation.

In a more preferred method according to the present invention, no emission intensity of said first dye is measurable, if said first dye is a non-fluorescent dye.

Alternatively, the first radiation measurement can be performed with the excitation and emission wavelength specific for the second dye, if both dyes are present in the unbound state.

A preferred method according to the present invention is a method, wherein said first radiation measurements of step b) is performed applying excitation wavelengths specific for said second dye and measuring the emission intensity of said second dye.

Moreover, it is possible to perform the first radiation measurement with the excitation wavelength specific for the first dye and the emission wavelength specific for the second dye, if both dyes are present in the unbound state.

Depending on the first radiation measurement, the second radiation measurement is preferably adapted, such that the same emission wavelength is measured in both measurements.

Another preferred method according to the present invention is a method, wherein said second radiation measurements of step c) is performed applying excitation wavelengths specific for said first dye and measuring the emission intensity of said second dye.

Yet another preferred method according to the present invention is a method, wherein said second radiation measurements of step c) is performed applying excitation wavelengths specific for said second dye and measuring the emission intensity of said second dye.

Consequently, if the second radiation measurement is based on the wavelength specific for the second dye, it is preferred that also the first radiation measurement is based on the same wavelength specific for the second dye. Dye combinations of this embodiment are, e.g., the dye/dye combination (see FIG. 1a/i) or the non-fluorescent dye/dye combination (see FIG. 1a/iii).

Still another preferred method according to the present invention is a method, wherein said second radiation measurements of step c) is performed applying excitation wavelengths specific for said first dye and measuring the emission intensity of said first dye.

Consequently, if the first radiation measurement is based on the excitation wavelength specific for the first dye, it is preferred that also the second radiation measurement is based on the same excitation wavelength specific for the first dye. Dye combinations of this embodiment are, e.g., the dye/quencher combination (see FIG. 1a/ii).

Still another aspect of the present invention is a method of verifying the composition ratio of two components according to the present invention, said method comprises the steps a) mixing the two components, wherein the first component comprises the first dye having said first affinity group and the second component comprises the second dye having said second affinity group, b) performing a first radiation measurement upon excitation with excitation light under conditions such that said first dye and said second dye are bound, said first fluorescence measurement is performed applying excitation wavelengths specific for said second dye and measuring the emission intensity of said second dye and c) performing a second radiation measurement upon excitation with excitation light under conditions such that said first dye and said second dye are bound, said second fluorescence measurement is performed applying excitation wavelengths specific for said first dye and measuring the emission intensity of said second dye, and d) comparing the two radiation measurements of step b) and c) to verify the composition ratio of said two components.

In this embodiment of the method of verifying the composition ratio of two components according to the present invention, both radiation measurements are performed with the affinity groups in the bound state (see FIG. 1b). Since the energy transfer occurs only in one direction, it is possible to measure one of the dyes independently from the other even in the bound state.

In a preferred method according to the present invention, said binding between said first dye having said first affinity group and said second dye having said second affinity group is irreversible.

Since the dyes are in the bound state for both radiation measurements, it is possible, but not essential that the binding between the two affinity groups is irreversible.

Yet another aspect of the present invention is a method of verifying the composition ratio of two components using the kit according to the present invention, said method comprises the steps a) mixing the two components, wherein the first component comprises the fluorescent dye having said first affinity group and the second component comprises the aromatic or heteroaromatic structure having said second affinity group, b) performing a first radiation measurement upon excitation with excitation light under conditions such that said fluorescent dye and said aromatic or heteroaromatic structure are not bound to each other via said affinity groups, said first radiation measurements is performed applying excitation wavelengths specific for said fluorescent dye and measuring the emission intensity of said fluorescent dye, c) performing a second radiation measurements upon excitation with excitation light under conditions such that said fluorescent dye and said aromatic or heteroaromatic structure are bound to each other via said affinity groups, said second radiation measurements is performed applying excitation wavelengths specific for said fluorescent dye and measuring the emission intensity of said fluorescent dye, and d) comparing the two radiation measurements of step b) and c) to verify the composition ratio of said two components.

A preferred method according to the present invention is a method, wherein said first radiation measurements of step b) is performed with said first component prior to mixing the two components in step a).

Another preferred method according to the present invention is a method, wherein said first radiation measurements of step b) is performed at composition parameters such that the binding between said first affinity group and said second affinity group is prevented.

EXAMPLE 1

PCR Setup with Two Component Solutions Containing the Two Control Components

Component Mixes

A) A 2-fold concentrated master mix composed of:
'RealTime ready DNA Master, Probes', a reagent mix for real-time PCR (Roche Applied Science, cat no. 05502381001), including 4 µM oligonucleotide according to SEQ ID NO: 3 terminally labeled at the 5'-end with a long wavelength fluorescent dye (JA286, Roche Applied Science; excitation maximum at 686 nm, emission maximum at 703 nm).

Structure of the JA286 dye 1 ng/µl of human cDNA (qPCR Human Reference cDNA, Clontech, cat. no. 639654)

B) A 2-fold concentrated detection mix specific for the GAPDH gene from human cDNA containing the following components:
1 µM each of human GAPDH primers according to SEQ ID NO: 1 and SEQ ID NO: 2
0.8 µM of a human GA PDH UPL probe (Universal Probe Library, Probe #60, Roche Applied Science, cat. no. 04688589001)
4 µM oligonucleotide according to SEQ ID NO: 4 terminally labeled at the 3'-end with the non-fluorescent quencher Dabsyl (Roche Applied Science, WO 2007/059816, synthesized by using commercially available Dabsyl CPG).

The two oligonucleotides according to SEQ ID NO: 3 and SEQ ID NO: 4 are complementary.

Setup of Multiwell PCR Plate

To demonstrate the effect of different ratios of the two component solutions of the reaction mixture in the control measurement, different combinations of master mix A and detection mix B were dispensed into a 1536-well PCR plate (Roche Applied Science, cat. no. 05358639001) using a Nanodrop Express liquid handling robot (Innovadyne, Part No. 12043 (Fluidics Module) and 11245 (Stage Module).

| Combination # | 2x master mix A [µl] | 2x detection mix B [µl] |
| --- | --- | --- |
| 1 | 0 | 1 |
| 2 | 0.5 | 1 |
| 3 | 1 | 1 |
| 4 | 1 | 0.5 |
| 5 | 1 | 0 |
| 6 | 0 | 0 |
| 7 | 0.5 | 0.5 |

Each combination was dispensed into 96 positions of the 1536 well plate representing technical replicates.

PCR Protocol and Control Measurement

Real-time amplification and pipetting control measurements were performed on a LightCycler 1536 instrument with the provided analysis software (Roche Applied Science).

Real-Time PCR:

Amplification was performed using the filter combination 465 (excitation)/510 (emission).

| | Cycles | Temp. (° C.) | Hold Time (sec) | Ramp Rate (° C./sec) | Acquisition |
| --- | --- | --- | --- | --- | --- |
| denaturation | 1 | 95 | 60 | 4.8 | none |
| amplification | 45 | 95 | 0 | 4.8 | none |
| | | 60 | 30 | 2.5 | single |
| cooling | 1 | 40 | 30 | 2.5 | none |

Control Measurement:

Two single acquisitions were performed using the filter combination 618 (excitation)/660 (emission).

| | Cycles | Temp. (° C.) | Hold Time (sec) | Ramp Rate (° C./sec) | Acquisition |
| --- | --- | --- | --- | --- | --- |
| 1. acquisition | 1 | 55 | 10 | 4.8 | single |
| 2. acquisition | 1 | 37 | 10 | 2.5 | single |

The ratio of the high temperature acquisition and the low temperature acquisition was calculated for each well of the reaction plate.

Figure 2:
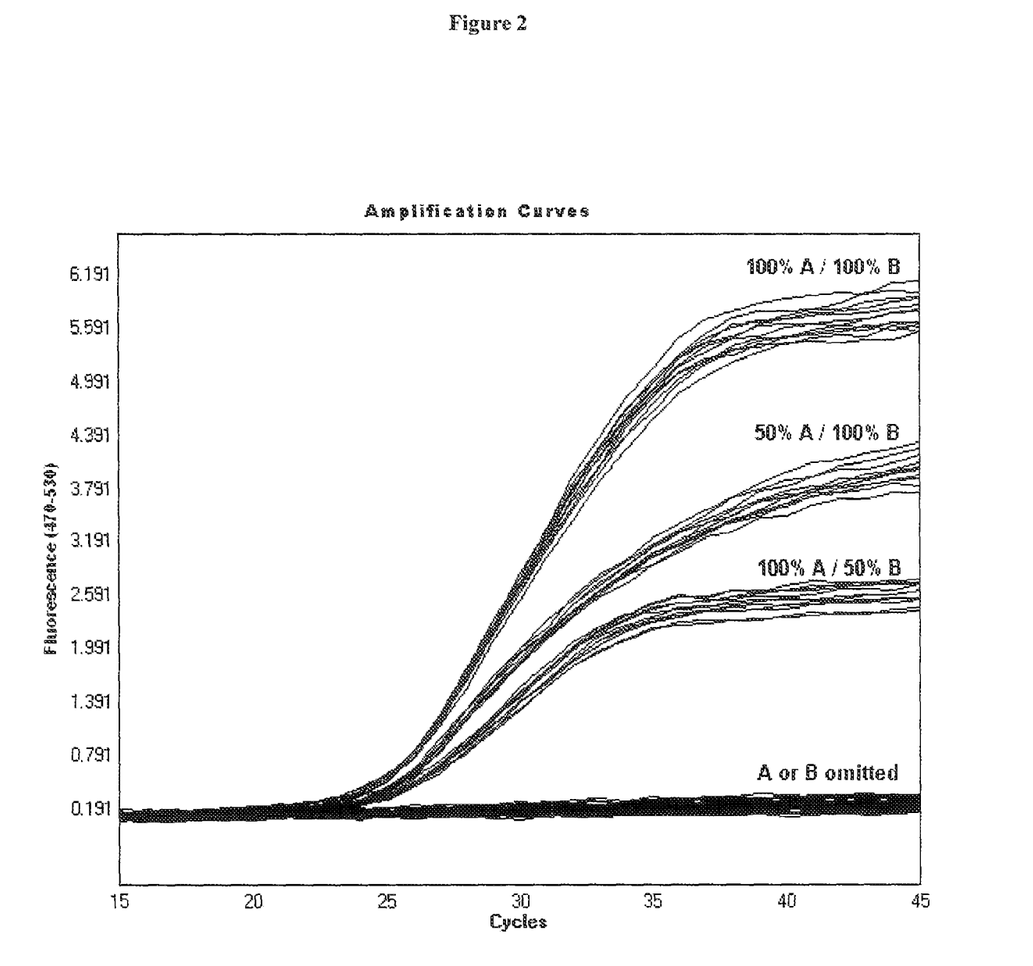
FIG. 2 Amplification curves for different compositions of two component.

Results:

With the 50% reduced portions of one of the two component solutions the amplification curves were still evaluable, but the PCR performance began to decrease (see FIG. 2). With an omitted component, results were negative.

Figure 3:
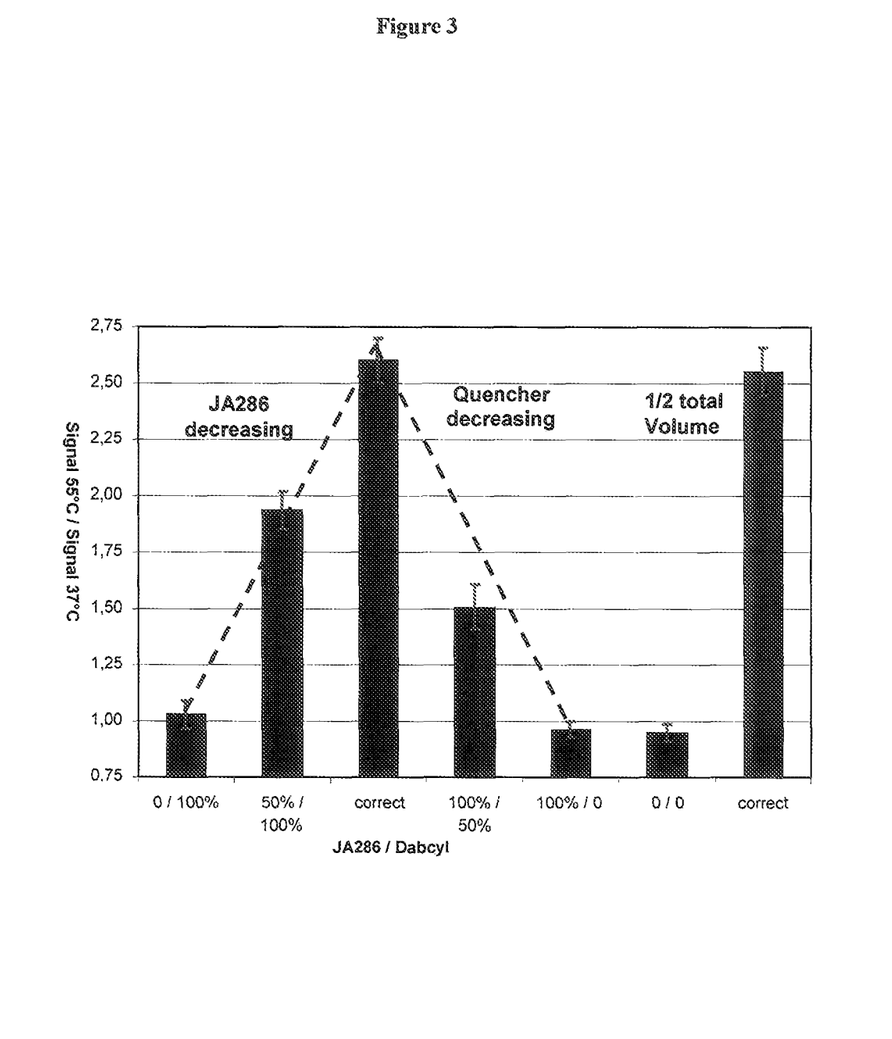
FIG. 3 Experimental performance based on two controls for different compositions of two component.

The ratio of the control measurements indicated clearly the lack of a component. The more one of the two component solutions was reduced, the lower was the calculated ratio (see FIG. 3). By setting a cutoff for the ratio (for this experiment at a value of 2 for example), all wells with a simulated pipetting error leading to invalid results will show a ratio below the cutoff and can be marked in a result table. With a reduced reaction volume but correct portions of the components, PCR results and control ratio were both not influenced.

EXAMPLE 2

Usage of Different Quencher Molecules for the Second Control Component

To proof the performance of the described control concept with various dyes or quencher molecules, the temperature dependent change in the fluorescence signal was shown for different available quenchers.

Reaction Mixture Composed of:
- 'RealTime ready DNA Master, Probes' (Roche Applied Science, cat no. 05502381001), including 2 µM oligonucleotide according to SEQ ID NO: 3 terminally labeled at the 5'-end with a long wavelength fluorescent dye (JA286, Roche Applied Science; excitation maximum at 686 nm, emission maximum at 703 nm, see Example 1).
- 2 µM oligonucleotide according to SEQ ID NO: 4, terminally labeled at the 3'-end with one of the following alternative quenchers:
  - Dabsyl
  - Dabcyl
  - BHQ-2
  - 3× additional dG
  - 3× deaza dG
  - JA286 (for dye self quenching)
  - no quencher control Protocol 10 µl of each of the 7 mixtures were pipetted into a 384-well PCR plate (Roche Applied Science, cat. no. 04729749001), and fluorescence was measured with a rising temperature gradient in a LightCycler 480 instrument (Roche Applied Science, cat. no. 05015243001).

Filter combination 618 (excitation)/660 (emission).

|  | Temp. (° C.) | Hold Time (sec) | Ramp Rate (° C./sec) | Acquisition | Acq/ ° C. |
|---|---|---|---|---|---|
| Melting curve | 20 | 10 | 4.8 | none | — |
|  | 95 | — | 0.11 | continuous | 5 |

Results

Figure 4:
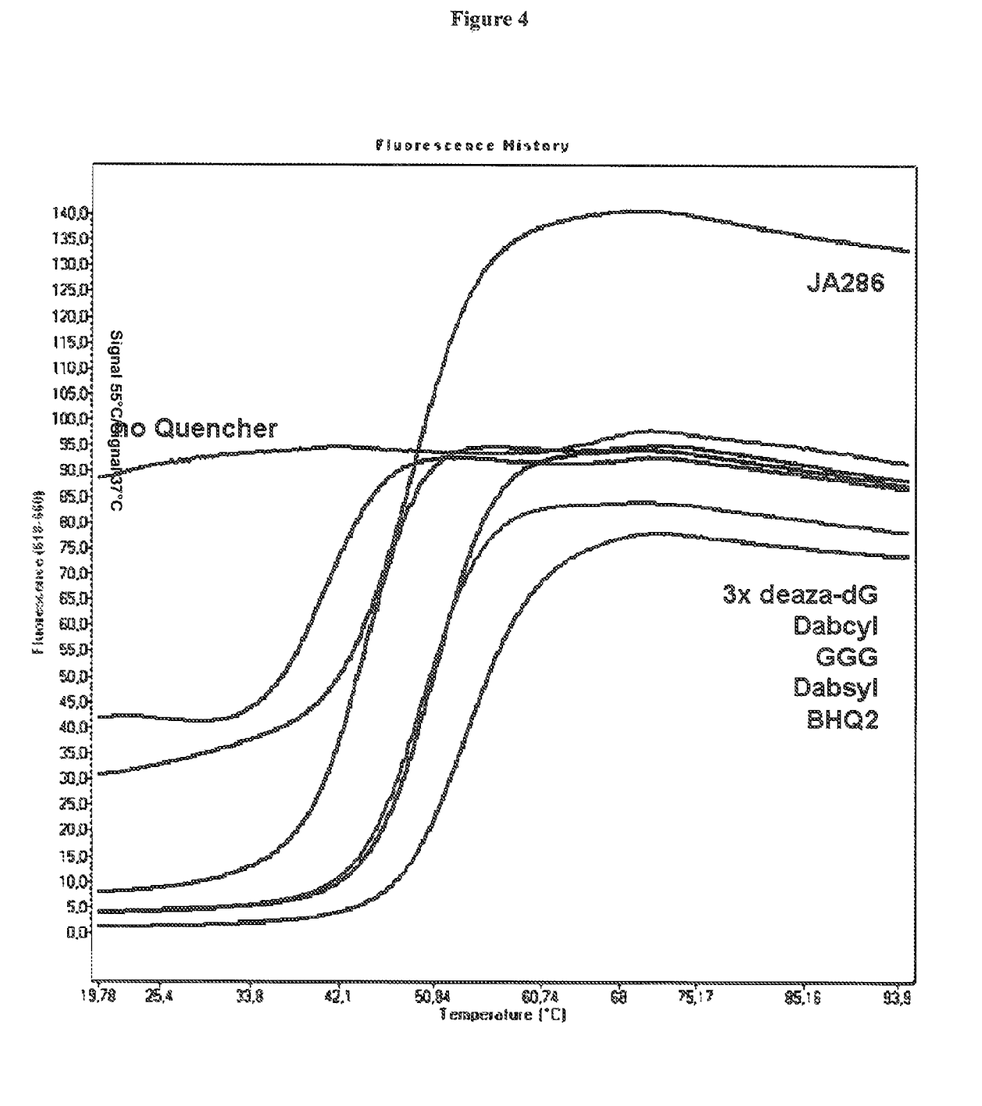
FIG. 4 Comparison of different quencher molecules.

With all the tested quenchers a substantial increase of the fluorescence was observed when the melting temperature of the oligonucleotide was exceeded and the binding of the first dye component to the second quencher component was ceased (see FIG. 4). So all these quenchers would be suited for the control concept with two measurements at different temperatures in the bound and the unbound state.

EXAMPLE 3

Usage of a Non-Fluorescent Dye for the Second Control Component

In this method the control measurements are at constant temperature at the same fluorescence detection wavelength but with two different excitation wavelengths. The dye in the first component can be measured with direct excitation. When the non-fluorescent dye (see US 2007/0077588) of the second component is bound to the first dye via the affinity groups, this combination is measured with excitation of the non-fluorescent dye at a short wavelength with no direct excitation of the first dye. But fluorescence emission of the first dye occurs due to energy transfer from the excited non-fluorescent dye to the first dye in close proximity.

Component Mixes
- A) 2-fold concentrated component A composed of
  - 'RealTime ready DNA Master, Probes', a reagent mix for real-time PCR (Roche Applied Science, cat no. 05502381001), including 4 µM oligonucleotide according to SEQ ID NO: 3 terminally labeled at the 5'-end with a long wavelength fluorescent dye (JA286, Roche Applied Science; excitation maximum at 686 nm, emission maximum at 703 nm, see Example 1).
- B) 2-fold concentrated component B containing:
  - 4 µM oligonucleotide according to SEQ ID NO: 4 terminally labeled at the 3'-end with the non-fluorescent dye (4',5'-dimethoxy-5-carboxyfluorescein (5-DmF)).

The two oligonucleotides according to SEQ ID NO: 3 and SEQ ID NO: 4 are complementary.

Setup of Multiwell PCR Plate

To demonstrate the effect of different amounts of the two component solutions of the reaction mixture in the control measurement, different amounts of component A and component B were pipetted into wells of a 384-well PCR plate (Roche Applied Science, cat. no. 04729749001).

| Combination # | Component A [µl] | Component B [µl] |
|---|---|---|
| 1 | 0 | 5 |
| 2 | 1.25 | 5 |
| 3 | 2.5 | 5 |
| 4 | 3.75 | 5 |
| 5 | 5 | 5 |
| 6 | 7.5 | 5 |
| 7 | 5 | 0 |
| 8 | 5 | 1.25 |
| 9 | 5 | 2.5 |
| 10 | 5 | 3.75 |
| 11 | 5 | 5 |
| 12 | 5 | 7.5 |

Each combination was dispensed into 96 positions of the 1536 well plate representing technical replicates.

Protocol

Fluorescence was measured in a LightCycler 480 instrument (Roche Applied Science, cat. no. 05015243001) at a constant temperature.

Filter combinations 618 (excitation)/660 (emission) and 498/660.

| | Cycles | Temp. (° C.) | Hold Time (sec) | Ramp Rate (° C./sec) | Acqui-sition |
|---|---|---|---|---|---|
| Acquisition | 1 | 40 | 10 | 4.8 | single |

Results

Figure 5:
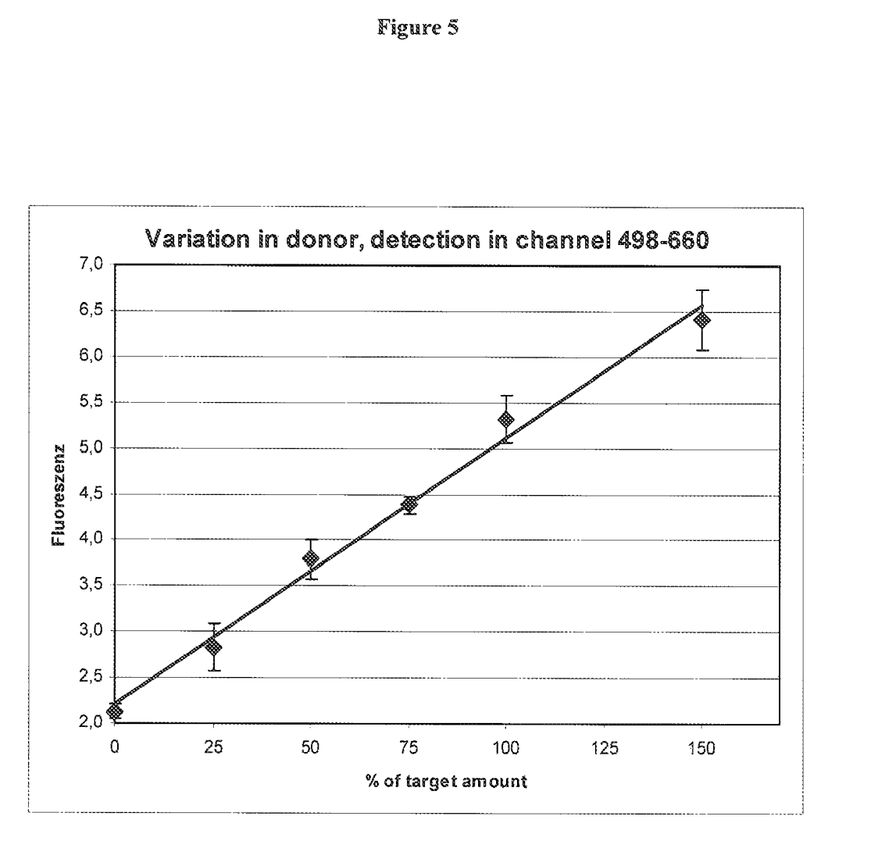
FIG. 5 Amount variation of the non-fluorescent dye in an embodiment using a non-fluorescent dye and a fluorescent dye.
Figure 6:
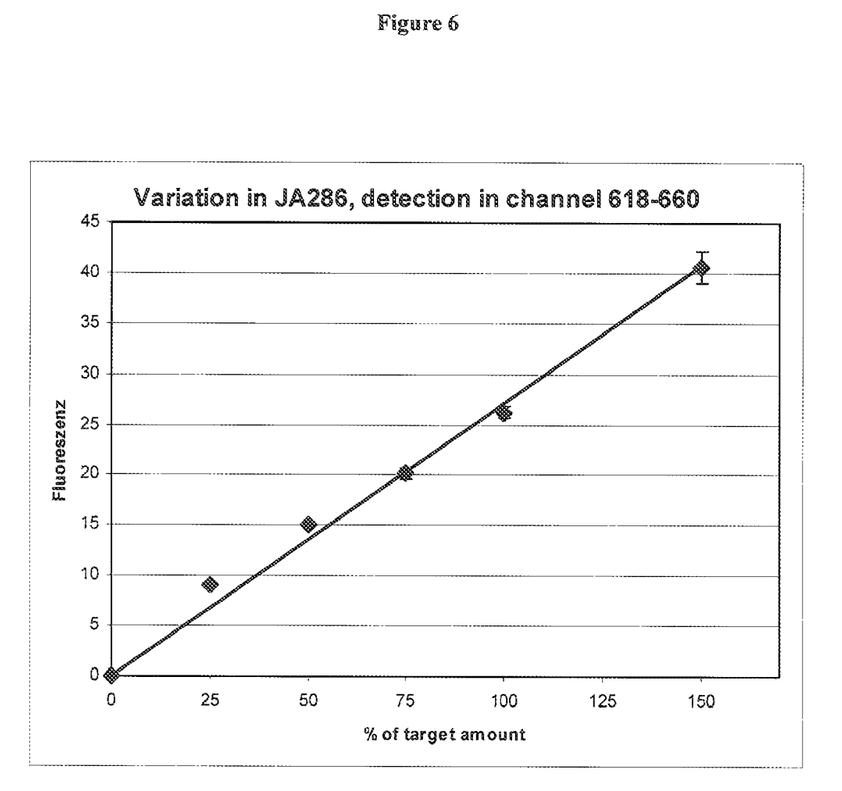
FIG. 6 Amount variation of the a fluorescent dye in an embodiment using a non-fluorescent dye and a fluorescent dye.

The signal from direct excitation of the first dye (618/660) demonstrates a correlation with the different amounts of component A and the signal from excitation via the non-fluorescent dye (498/660) demonstrates a correlation with the portion of component B in presence of a constant amount of component A (see FIGS. 5 and 6).

EXAMPLE 4

Usage of dig/Anti-dig as Affinity Groups for the Two Components

To proof the performance of the described control concept with various affinity groups, digoxigenin (DIG) and an anti-digoxigenin antibody (anti-DIG) were used as affinity groups for the dyes JA286 and the non-fluorescent dye (refer to example 3). For measurement, the solution was excited at the absorption wavelength of the non-fluorescent dye and fluorescence was detected at the emission wavelength of the acceptor dye.

Component Mixes

A) 2-fold concentrated component A containing:
4 μM DIG labeled with the long wavelength fluorescent dye JA286 (Roche Applied Science; excitation maximum at 686 nm, emission maximum at 703 nm, see Example 1), in 10 mM Tris pH8.3 and 3 mM MgCl2.

B) 2-fold concentrated component B containing:
4 μM anti-DIG antibody (Roche Applied Science) labeled with the non-fluorescent dye (Roche Applied Science), in 10 mM Tris pH8.3 and 3 mM MgCl2.

Setup of Multiwell PCR Plate

To demonstrate the effect of a lack of one of the two component solutions in the control measurement, different amounts of component A and component B were pipetted into wells of a 384-well PCR plate (Roche Applied Science, cat. no. 04729749001).

| Combination # | Component A [μl] | Component B [μl] |
|---|---|---|
| 1 | 0 | 5 |
| 2 | 5 | 5 |
| 3 | 5 | 0 |
| 4 | 0 | 0 |

Each combination was dispensed into 10 positions of a 384-well plate representing technical replicates.

Protocol

Fluorescence was measured in a LightCycler 480 instrument (Roche Applied Science, cat. no. 05015243001) at a constant temperature.

Filter combination: 498 (excitation)/660 (emission).

| | Cycles | Temp. (° C.) | Hold Time (sec) | Ramp Rate (° C./sec) | Acqui-sition |
|---|---|---|---|---|---|
| Acquisition | 1 | 40 | 10 | 4.8 | single |

Results

Figure 7:
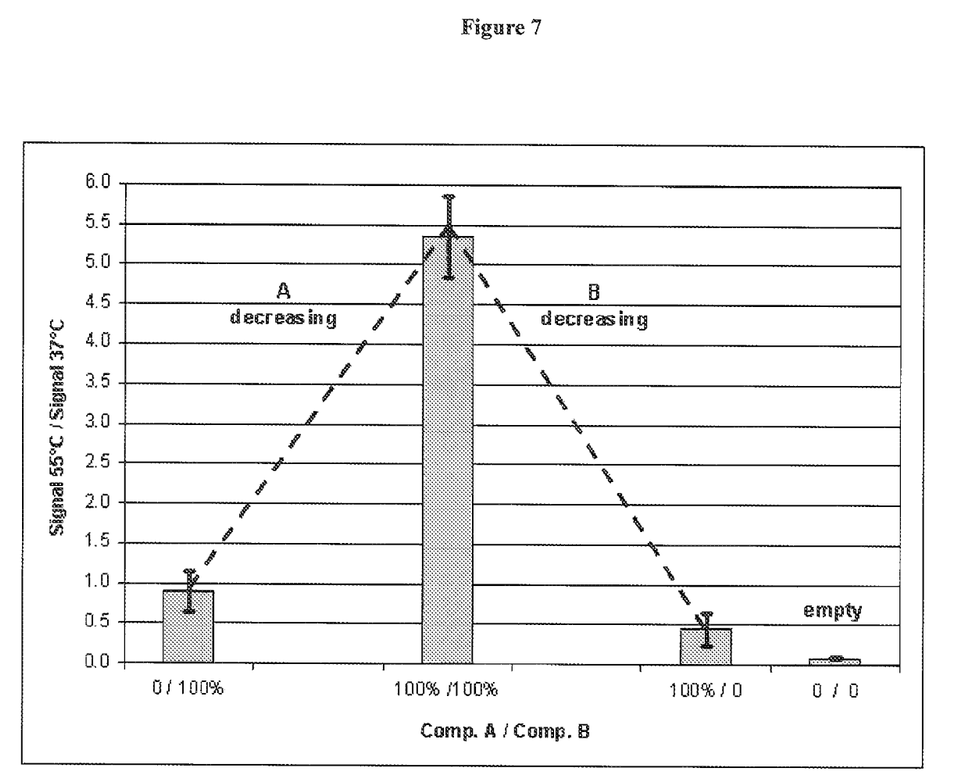
FIG. 7 Embodiment of the present invention using DIG/anti-DIG as affinity groups of a non-fluorescent dye and a fluorescent dye.

If the two components are present in the mixture, due to energy transfer from the excited donor to the acceptor dye, a fluorescence signal is measurable, which is significantly higher than the background signal that can be measured when one of the two components is omitted (see FIG. 7).

What is claimed is:

1. A kit for composition ratio control, the kit comprising:
a first dye having a first affinity group comprising a first oligonucleotide, the first dye being excitable by a first excitation light to emit radiation or to transfer energy to a second dye; and
a second dye having a second affinity group comprising a second oligonucleotide, the second dye being excitable by a second excitation light or by energy transfer from the first dye, the first and the second oligonucleotides each comprise an L-nucleotide, wherein the first and the second affinity group have affinity to bind to each other, whereby energy transfer between the dyes is enabled upon binding, and
wherein a mixture of the first dye and the second dye emits radiation upon excitation with the first or the second excitation light, whereby the radiation is a measure for the composition ratio of the first and the second dye.

2. The kit of claim 1, wherein the first dye is a fluorescent dye and the second dye is a quencher molecule, the quencher molecule being excitable by energy transfer from the fluorescent dye upon binding of the affinity groups, whereby the quencher molecule prevents fluorescence emission of the fluorescent dye.

3. The kit of claim 2, wherein the fluorescent dye and the quencher molecule are the same molecule.

4. The kit of claim 1, wherein the first and the second affinity group comprise an equal number of nucleotides.

5. The kit of claim 1, wherein the second affinity group is provided in a same concentration as the first affinity group.

6. A method of verifying a composition ratio of two components, the method comprising the steps of:
mixing together a first component comprising the first dye of the kit of claim 1 and a second component comprising the second dye of the kit of claim 1, wherein the first and second affinity groups have affinity to bind to each other whereby energy is transferred between the dyes and radiation is emitted, the radiation being a measure of the composition ratio of the first and second dyes;
performing a first radiation measurement after excitation with excitation light under conditions such that the first dye and the second dye do not bind to each other via their affinity groups;
performing a second radiation measurement after excitation with excitation light under conditions such that the first dye and the second dye bind to each other via their affinity groups, and
comparing the first and second radiation measurements to verify the composition ratio of the first component and the second component.

7. The method of claim 6, wherein the first radiation measurement is performed with the first component prior to mixing together the first component and the second component.

8. The method of claim 6, wherein the first radiation measurement is performed by applying excitation wavelengths specific for the first dye and measuring an emission intensity of the first dye.

9. The method of claim 6, wherein the first radiation measurement is performed by applying excitation wavelengths specific for the second dye and measuring an emission intensity of the second dye.

10. The method of claim 6, wherein the second radiation measurement is performed by applying excitation wavelengths specific for the first dye and measuring an emission intensity of the second dye.

11. The method of claim 6, wherein the second radiation measurement is performed by applying excitation wavelengths specific for the first dye and measuring an emission intensity of the first dye.

12. A method of verifying a composition ratio of two components, the method comprising the steps of:
mixing a first component comprising the first dye of the kit of claim 1 and a second component comprising the second dye of the kit of claim 1, wherein the first dye is a fluorescent dye and the second dye is a fluorescent dye having an excitation maximum at a longer wavelength than the first dye, and wherein the second dye is excitable by energy transfer from the first dye such that the second dye emits fluorescence light having a wavelength different from that of the first dye;
performing a first radiation measurement upon excitation with excitation light under conditions such that the first dye and the second dye are bound via their affinity groups, wherein the first radiation measurement is performed by applying excitation wavelengths specific for the second dye and measuring the emission intensity of the second dye;

performing a second radiation measurement upon excitation with excitation light under conditions such that the first dye and the second dye are bound via their affinity groups, wherein the second radiation measurement is performed by applying excitation wavelengths specific for the first dye and measuring the emission intensity of the second dye, and comparing the first and second radiation measurements to verify the composition ratio of the first and second components.

13. A method of verifying a composition ratio of two components, the method comprising the steps of:

mixing together a first component and a second component, wherein the first component comprises the first dye of the kit of claim 1, wherein said first dye is fluorescent and the second component comprises the second dye of the kit of claim 1, wherein said second dye is an aromatic or heteroaromatic molecule;

performing a first radiation measurement after excitation with excitation light under conditions such that the fluorescent dye and the aromatic or heteroaromatic molecule are not bound to each other via their affinity groups, the first radiation measurement performed by applying excitation wavelengths specific for the fluorescent dye and measuring the emission intensity of the fluorescent dye;

performing a second radiation measurement after excitation with excitation light under conditions such that the fluorescent dye and the aromatic or heteroaromatic molecule are bound to each other via their affinity groups, the second radiation measurement performed by applying excitation wavelengths specific for the fluorescent dye and measuring the emission intensity of the fluorescent dye, and comparing the first and second radiation measurements to verify the composition ratio of the two components.

14. The method of claim 13, wherein the first radiation measurement is performed with the first component prior to mixing together the two components.

\* \* \* \* \*